United States Patent [19]

Liepmann et al.

[11] 4,271,193

[45] Jun. 2, 1981

[54] N1-BENZOYL-N2-PHENYLDIAMINO-PROPANOLS AND PHARMACEUTICAL COMPOSITIONS THEREOF, AND PROCESSES FOR THEIR PREPARATION

[75] Inventors: Hans Liepmann; Rolf Hueschens, both of Hanover; Wolfgang Milkowski, Burgdorf; Horst Zeugner; Henning Heinemann, both of Hanover; Klaus-Ulrich Wolf, Haenigsen; Insa Hell; Reinhard Hempel, both of Hanover, all of Fed. Rep. of Germany

[73] Assignee: Kali-Chemie Pharma GmbH, Hanover, Fed. Rep. of Germany

[21] Appl. No.: 51,227

[22] Filed: Jun. 22, 1979

[30] Foreign Application Priority Data

Jun. 24, 1978 [DE] Fed. Rep. of Germany ....... 2827801

[51] Int. Cl.³ .................. A61K 31/335; A61K 31/36; A61K 31/165
[52] U.S. Cl. ................................ 424/324; 260/340.3; 260/340.5 R; 424/278; 424/282
[58] Field of Search ............ 260/559 S, 559 R, 340.3, 260/340.5 R; 424/324, 282, 278

[56] References Cited

U.S. PATENT DOCUMENTS 3,998,809  12/1976  Milkowski et al. .............. 260/239 B

FOREIGN PATENT DOCUMENTS 2336399  7/1972  Fed. Rep. of Germany ........... 424/324
2720908  11/1978  Fed. Rep. of Germany ........... 424/324
2720968  11/1978  Fed. Rep. of Germany ........... 424/324

Primary Examiner—Frederick E. Waddell
Attorney, Agent, or Firm—Schwartz, Jeffery, Schwaab, Mack, Blumenthal & Koch

[57] ABSTRACT $N_1$-benzoyl-$N_2$-phenyl-1,3-diaminopropan-2-ols are disclosed which exhibit a stabilizing effect on the gastric mucosa and enhance the stability and resistance of the gastic mucosa against harmful effects caused by, e.g., excessive alcohol consumption or drugs. The compounds are useful in the prophylaxis and treatment of gastritis.

Further disclosed are pharmaceutical compositions which are effective in stabilizing the gastric mucosa and in the treatment and proplylaxis of gastritis and which comprise as a pharmacologically active ingredient $N_1$-benzoyl-$N_2$-phenyl-1,3-diaminopropan-2-ols, or a pharmaceutically acceptable acid addition salt thereof, and a pharmaceutically acceptable diluent. Further disclosed are processes for the preparation of the $N_1$-benzoyl-$N_2$-phenyl-1,3-diaminopropan-2-ols.

24 Claims, No Drawings

N1-BENZOYL-N2-PHENYLDIAMINO-PROPANOLS AND PHARMACEUTICAL COMPOSITIONS THEREOF, AND PROCESSES FOR THEIR PREPARATION

BACKGROUND OF THE INVENTION

The present invention relates to new $N_1$-benzoyl-$N_2$-phenyl-1,3-diaminopropan-2-ol derivatives and pharmaceutically acceptable salts thereof, processes for their preparation, pharmaceutical compositions thereof and methods of medical treatment using same.

The $N_1$-benzoyl-$N_2$-phenyl-1,3-diaminopropan-2-ol derivatives according to the present invention fall within the scope of general formulae of chemical intermediates which are disclosed in the U.S. Pat. No. 3,998,809 and the German Offenlegungsschrift No. 2 221 558. Yet, these compounds are not specifically disclosed in these prior art publications. The German Offenlegungsschrift and the U.S. Pat. No. 3,998,809 disclose that the $N_1$-benzoyl-$N_2$-phenyl-1,3-diaminopropan-2-ol derivatives are valuable intermediates for the preparation of benzodiazepine- and benzodiazocine derivatives which are pharmacologically effective in influencing the central nervous system and which due to these properties are useful as tranquilizers, sedatives, or anticonvulsive agents. Yet, no independent pharmacological activity of these intermediates has been disclosed.

It is well known in the medical art that the gastro-intestinal mucosa can be severely damaged by various harmful influences e.g., due to duodeno-gastric reflux, excessive alcohol consumption or due to side effects of a medical treatment with non-steroid antiphlogistic agents, with steroids or with chemotherapeutic agents. The problems involved with a disturbed mucous barrier have been described, e.g., by W. F. Caspary in D.Med.-Wochenschrift 100 (1975) pages 1263–1268 and by H. S. Murray et al in Brit. Med. J. I No. 5896 (1974) pages 19-20.

A causal treatment of the above conditions and related diseases, e.g., gastritis, has so far not been possible.

The conventionally used therapeutic methods essentially provide only a symptomatic relief and are directed towards reducing the aggressive agents (hydrochloric acid, pepsin), e.g., by means of antacid agents. Anti-acidic agents do not have a healing effect. Their therapeutical effect is limited primarily to a pain-reducing component.

SUMMARY OF THE INVENTION

It is an object of the present invention to provide new pharmacologically active compounds and pharmaceutical compositions which are effective in stabilizing the gastro-intestinal mucosa and enhancing its resistance against various harmful effects and which are effective in the treatment or prophylaxis of acute and chronic gastritis in larger mammals, in particular human beings.

It is a further object of this invention to provide such compounds and compositions which exhibit a direct causal therapeutic effect on the disturbed gastro-intestinal mucosa.

It is a further object of the present invention to provide such compounds and compositions, which are low in side effects and toxicity and exhibit a large therapeutic index.

It is a further object of the present invention to provide such compounds and compositions which promote the redressing of the disturbed physiological balance at the mucous membrane and the regeneration of the impaired mucous membrane.

It is a further object of the present invention to provide a method of treatment of physiological disorders which are connected with the development of gastritis, in particular a method for prophylaxis and treatment of acute and chronic gastritis.

It is a further object of the present invention to provide processes for preparing pharmacologically active compounds which are effective in preventing and/or healing of gastritis.

In order to accomplish the foregoing objects according to the present invention, there are provided new compounds selected from the group of $N_1$-benzoyl-$N_2$-phenyl-1,3-diaminopropan-2-ols, having the formula I

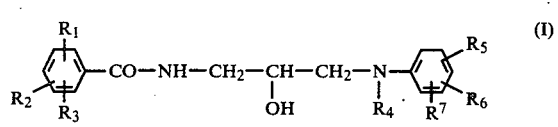

wherein $R_1$, $R_2$ and $R_3$ are the same or different from each other and each represents hydroxy, benzyloxy, chlorbenzyloxy or alkoxy containing 1 to 4 carbon atoms;

or $R_1$ is as defined above and $R_2$ and $R_3$ together represent methylenedioxy or ethylenedioxy;

or $R_1$ and $R_2$ represent methoxy and $R_3$ represents acetoxy, allyloxy, propargyloxy, methoxycarbonyloxy or ethoxycarbonyloxy;

$R_4$ represents hydrogen, alkyl containing 1 to 4 carbon atoms, $\beta$-hydroxyethyl, or $\beta$-methoxyethyl, and $R_5$ and $R_6$ and $R_7$ are the same or different from each other and $R_5$ and $R_6$ each represents hydrogen, fluorine, chlorine, bromine, iodine, alkyl containing 1 to 4 carbon atoms, or alkoxy containing 1 to 4 carbon atoms;

or $R_5$ and $R_6$ together represent methylenedioxy or ethylenedioxy, and $R_7$ represents hydrogen, fluorine, chlorine, bromine, iodine, alkyl containing 1 to 4 carbon atoms, or alkoxy containing 1 to 4 carbon atoms, trifluoromethyl or nitro; with the proviso that if $R_1$, $R_2$ and $R_3$ each represents methoxy and are situated in 3, 4 and 5 position and $R_4$ is methyl no more than 2 of the substituents $R_5$, $R_6$ and $R_7$ represent hydrogen and pharmaceutically acceptable salts thereof.

It has now been found that the compounds of formula (I) and their pharmaceutically acceptable salts as such possess valuable pharmacological and therapeutic properties. In particular they exhibit a stabilizing effect on the gastro-intestinal mucosa against various harmful effects of, e.g., other pharmacologically active agents or excessive amounts of alcohol, and thus are useful in the prevention and treatment of acute and chronic gastritis.

According to the present invention, there are further provided pharmaceutical compositions comprising an effective amount of at least one compound selected from the group $N_1$-benzoyl-$N_2$-phenyl-1,3-diaminopropan-2-ols, having the formula (I) and pharmaceutically acceptable salts thereof, which are effective in stabilizing the gastro-intestinal mucosa and a pharmaceutically acceptable diluent.

According to the present invention, there is further provided a method of preventing and treating disorders of the gastro-intestinal mucosa which are connected with the consumption of drugs having adverse side effects on the gastro-intestinal mucosa, and in particular a method of preventing and treating gastritis in larger mammals, in particular human beings, which comprises the step of administering the above-described pharmaceutical composition.

According to the present invention, there are further provided processes for preparing the compounds of formula (I) in good yields.

According to the present invention the $N_1$-benzoyl-$N_2$-phenyl-1,3-diaminopropan-2-ols of formula (Ia) can be prepared by first preparing a compound of formula Ia

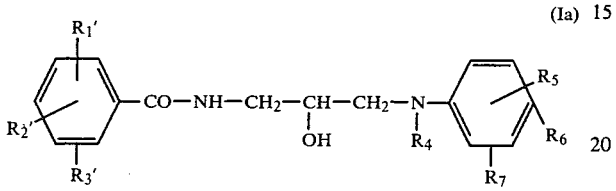

wherein
$R_4$, $R_5$, $R_6$ and $R_7$ are as defined above, and
$R_1'$, $R_2'$, and $R_3'$ are the same or different from each other and each represents benzyloxy, chlorobenzyloxy or alkoxy containing 1 to 4 carbon atoms; or
$R_1'$ is as defined above; and
$R_2'$ and $R_3'$ together represent methylenedioxy or ethylenedioxy; or
$R_1'$ and $R_2'$ represent methoxy; and
$R_3'$ represents acetoxy, methoxycarbonyloxy or ethoxycarbonyloxy, which comprises the step of reacting a 1,3-diaminopropan-2-ol having the formula II

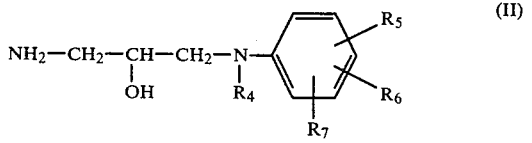

wherein
$R_4$, $R_5$, $R_6$ and $R_7$ are as defined above with a reactive benzoyl derivative having the formula III

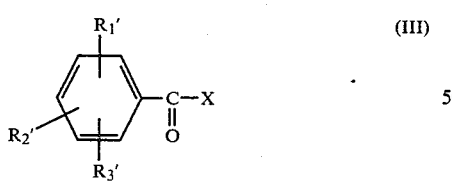

wherein
$R_1'$, $R_2'$ and $R_3'$ are as defined above.

According to the present invention compounds of formula (I) wherein $R_1$, $R_2$ and/or $R_3$ represent hydroxy are prepared by hydrogenolytically debenzylating a compound of formula (Ia) wherein $R_1$, $R_2$ and/or $R_3$ represent benzyloxy or chlorobenzyloxy, or by alkaline hydrolysis of a compound of formula (I) wherein $R_3$ represents acetoxy, methoxycarbonyloxy or ethoxycarbonyloxy.

Furthermore, in compounds of formula (I) wherein at least one of the substituents $R_1$, $R_2$ and $R_3$ is hydroxy, the hydroxy group can be substituted to form an etherified or esterified hydroxy group as set forth in the definition of $R_1$, $R_2$ and $R_3$. In particular, a hydroxy group can be transferred into the desired alkoxy, allyloxy, propargyloxy, and optionally also into the optionally substituted benzyl group as defined above.

Further, a compound of formula (I) wherein $R_4$ is alkyl can also be prepared by alkylating a compound of formula (I) wherein $R_4$ is hydrogen.

Further objects, features, and advantages of the present invention will become apparent from the detailed description of the invention, which follows.

DETAILED DESCRIPTION OF THE PREFERRED EMBODIMENTS

It has been found that the compounds of formula (I) and their pharmacologically acceptable salts possess novel pharmacological properties. In particular important is their ability to stabilize the gastro-intestinal mucosa against various harmful and irritating effects which may occur, caused, e.g., by duodeno-gastric reflux, excess consumption of alcohol and as a side effect of non-steroid anti-phlogistic agents, steroids and chemotherapeutic agents.

Due to their above-mentioned pharmacological properties the compounds of formula (I) according to the present invention and their pharmaceutically acceptable salts for the first time provide a means for causal therapy and prophylaxis of the damages of and disturbances at the gastro-intestinal mucosa under the above-mentioned harmful conditions. In particular, the compounds of formula (I) and pharmaceutically acceptable salts are useful in the medical art in the treatment and prophylaxis of acute and chronic gastritis.

If in the compounds of formula (I) the substituents $R_1$ to $R_7$ comprise an alkyl group containing 1 to 4 carbon atoms, this group may be straight or branched. Suitable alkyl groups, for example, are the following: methyl, ethyl, propyl, isopropyl, n-butyl or isobutyl. Suitable halogen atoms are fluorine, chlorine, bromine, iodine, in particular fluorine, chlorine and bromine.

In the compounds of formula (I), $R_4$ preferably represents methyl or hydrogen. Yet, it may also represent ethyl, propyl, or isopropyl or methoxyethyl.

In the compounds of formula (I), $R_1$, $R_2$ and $R_3$ preferably represent alkoxy, in particular methoxy, or alkylenedioxy groups.

In the compounds of formula (I), $R_5$, $R_6$ and $R_7$ preferably $R_5$, $R_6$ and $R_7$ represent hydrogen, halogen, trifluoromethyl, methoxy, or methyl, whereby hydrogen, chlorine and fluorine are most preferred. Preferably two of $R_5$, $R_6$ and $R_7$ are hydrogen and the other represents a substituent, preferably fluorine or chlorine, in the 4-position of the phenyl nucleus.

The new compounds of formula (I) and their pharmaceutically acceptable salts exhibit a stabilizing effect on the gastro-intestinal mucosa activity combined with a favorably large therapeutic index. They are low in side effects and toxicity.

The pharmacological properties of the compounds according to the present invention are demonstrated in the following pharmacological tests.

DESCRIPTION OF THE PHARMACOLOGICAL TEST METHODS

1. Acute toxicity

The acute 7-day toxicity is determined after a single application per os in white NMRI-mice which had not been fed. The calculation of the $LD_{50}$ is carried out by probitananalysis by means of electronic data processing (see L. Cavalli-Sforza, Gustav Fischer-Verlag, Stuttgart (1964), Grundbegriffe der Biometrie, p. 153).

2. Inhibition of loss of stomach epithelium cells

The test compound is orally administered to narcotized male rats of the breed SIV50 prior to the beginning of the test. Subsequently, acetylsalicylic acid is administered as an irritating agent in order to induce a pathologically increased loss of epithelium cells. In order to determine the induced total loss of cells in the rats stomach, acetylsalicylic acid is administered to animals without prior administration of a protective compound.

In order to prepare the animals for the determination, the trachea is laid free and a tube introduced therein. Subsequently, a laparotomy in the medial part, displacement of the stomach and introducing and fixing of a vein-catheter for recovering stomach juices are effected. By means of the introduced vein-catheter, stomach juice is recovered and then is centrifuged and microscopically analyzed.

The percent reduction of loss of cells induced by the acetylsalicylic acid after previous administration of 3 times 300 mg/kg of the test compound is determined.

For example, the following test compounds have been tested according to the above described methods:

(A) $N_1$-(3,4,5-trimethoxybenzoyl)-$N_2$-methyl-$N_2$-(4-fluorophenyl)-1,3-diaminopropan-2-ol
(B) $N_1$-(3,4,5-trimethoxybenzoyl)-$N_2$-methyl-$N_2$-(4-chlorophenyl)-1,3-diaminopropan-2-ol
(C) $N_1$-(3,4,5-trimethoxybenzoyl)-$N_2$-methyl-$N_2$-(4-trifluoromethylphenyl)-1,3-diaminopropan-2-ol
(D) $N_1$-(3,4,5-trimethoxybenzoyl)-$N_2$-methyl-$N_2$-(4-methylphenyl)-1,3-diaminopropan-2-ol
(E) $N_1$-(3,4,5-trimethoxybenzoyl)-$N_2$-ethyl-$N_2$-(4-fluorophenyl)-1,3-diaminopropan-2-ol
(F) $N_1$-(3,4,5-trimethoxybenzoyl)-$N_2$-(2,4,6-trimethylphenyl)-1,3-diaminopropan-2-ol
(G) $N_1$-(3,4,5-triethoxybenzoyl)-$N_2$-methyl-$N_2$-(4-fluorophenyl)-1,3-diaminopropan-2-ol
(H) $N_1$-(4-methoxy-2,3-ethylenedioxybenzoyl)-$N_2$-methyl-$N_2$-(4-fluorophenyl)-1,3-diaminopropan-2-ol
(I) $N_1$-(4-butoxy-3,4-dimethoxybenzoyl)-$N_2$-methyl-$N_2$-(4-fluorophenyl)-1,3-diaminopropan-2-ol As a standard control substance aluminum phosphate in gel-form has been used.

The results are shown in Table I below. From the data in Table I it is apparent that the compounds according to the present invention exhibit an outstandingly good stabilizing effect on the gastro-intestinal mucosa in the stomach. Furthermore, due to their low toxicity they possess a large therapeutic index.

TABLE I

| TEST COMPOUND | $LD_{50}$ p.o. (mg/kg) | % reduction of loss of epithelium cells in the stomach |
| --- | --- | --- |
| A | 5010 | 53 |
| B | >5000 | 77 |
| C | >1390 | 47.8 |
| D | >3160 | 47.8 |
| E | >1280 | 43 |
| F | >1270 | 28.4 |
| G | >1370 | 63 |
| H | >1230 | 48.6 |
| I | >1370 | 27.2 |
| S | >5000 | 8.5 |

Due to their above-mentioned pharmacological properties, the $N_1$-benzoyl-$N_2$-phenyl-1,3-diaminopropan-2-ols of formula (I) and their pharmaceutically acceptable salts, are useful in medical treatment, in particular in the treatment and prophylaxis of damages to the gastointestinal mucosa, in particular the treatment and prophylaxis of acute and chronic gastritis, and physiological disorders and conditions which favor the development of gastritis.

According to a feature of the invention, there are provided pharmaceutical compositions containing at least one of the compounds of formula (I) or their pharmaceutically acceptable salts. The compositions may take the form of solid or liquid formulations for enteral, preferably oral, or for parenteral administration. Thus, the pharmaceutical formulations may be in solid form, e.g., in the form of capsules, tablets, coated tablets, or suppositories, or in liquid form, e.g., in the form of solutions, suspensions, or emulsions. These formulations may comprise conventional inorganic and/or organic inert pharmaceutical carriers and adjuvants, which are suitable for enteral and/or parenteral administration. Thus, the pharmaceutical diluents may comprise solids and/or liquid carrier materials, such as, e.g., lactose, starch, gum arabic, gelatin, vegetable oils, fats, polyethylene glycols, and the like. If desired, the pharmaceutical compositions according to the present invention, may further comprise conventional additives, such as preserving agents, stabilizing agents, moisturizers, emulsifying agents, or salts, which serve for regulating the osmotic pressure or as a buffer.

Suitable carrier materials and adjuvants are well known in the pharmaceutical art and are disclosed and/or recommended as adjuvants in the pharmaceutical and cosmetic art and related arts in the following publications, the disclosure of which is hereby incorporated by reference:

Ullmanns Encyclopedia der technischen Chemie, Vol. 4, (1953), p. 1; Journal of Pharmaceutical Sciences, Vol. 52, (1963), p. 918; Dr. H. P. Fiedler, Lexikon der Hilfsstoffe fuer Pharmazie, Kosmetik und angrenzende Gebiete, Cantor KG, Aulendorf i. Wuertt. 1971.

The pharmaceutical formulations according to the present invention are prepared in any conventional manner, e.g., by dissolving the pharmacologically active agents in at least a portion of liquid carrier materials or by thoroughly mixing the pharmacologically active agents with at least a portion of the solid carrier materials, adding the remaining adjuvants and/or carrier materials, and formulating the resulting mixtures into the desired dosage form by known pharmaceutical methods, e.g., tabletting, molding into suppositories, or filling into capsules.

In the pharmaceutical compositions, according to the present invention, the amount of the pharmacologically active compound of formula (I) per single dosage unit may vary according to the type of the compound and the conditions to be treated. In pharmaceutical compositions for oral administration to adult humans, the amount of the compound of formula (I) per single dosage preferably is in the range of from about 50 to about 150 mg per single dosage unit.

The amount of compounds of formula (I) which suitably is applied for stabilizing the gastro-intestinal mucosa against harmful and irritating effects and for the treatment and prophylaxis of acute and chronic gastritis may, of course, vary according to the conditions to be treated and the mode of application. For oral application to adult persons, daily dosages of from about 150–450 mg are suitable.

According to the present invention, the compounds of formula (Ia) can be prepared by reacting an $N_1$-phenyl-1,3-diaminopropan-2-ol of formula (II) with an acid derivative of formula (III). This reaction suitably is carried out in an inert solvent. The reaction temperature preferably is between about $-10°$ and the boiling point of the reaction mixture, and the reaction may take place under normal pressure or under elevated pressure.

Preferably, the reaction is carried out in the presence of an acid-binding agent, for example, an inorganic base, such as an alkali metal carbonate or hydroxide, e.g., potassium carbonate, sodium carbonate, potassium hydroxide, or sodium hydroxide, or a tertiary organic amine, for example, triethylamine or pyridine. If an excess of such a tertiary organic amine is used, this amine simultaneously can serve as the inert solvent. Other suitable inert solvents are, e.g., methylene chloride, chloroform, acetone, tetrahydrofuran, dioxane, benzene, toluene, or chlorobenzene.

For preparing $N_1$-benzoyl-$N_2$-phenyl-1,3-diaminopropan-2-ols of formula (I) wherein at least one of the substituents $R_1$, $R_2$ and $R_3$ represents hydroxy, it is advisable to first react the 1,3-diaminopropan-2-ols of formula (II) with benzoyl derivatives of formula (III) wherein the hydroxy group is substituted by a protective group, such as, for example, benzyl, acetyl, or an alkoxy carbonyl group and to subsequently split off the protective group. The cleavage of protective groups can be done according to conventional methods. In the case of a benzyloxy group, for example, the benzyloxy group can be cleaved hydrogenolytically with hydrogen in the presence of a noble metal catalyst, such as, for example, palladium/charcoal, at a temperature of between about 15° and about 50° C. Suitable solvents for this reaction are lower alkyl alcohols, dioxane, tetrahydrofuran, or ethyl acetate. For cleaving the acetoxy group or an alkoxy carbonyloxy group, an alkaline hydrolysis can be carried out, for example, with sodium- or potassium-hydroxide or an aqueous solution of ammonia at temperatures of between about 25° and about 80° C. Hereby lower alkyl alcohols may be used as a solvent and the reaction may be carried out under an atmosphere of inert gas, such as nitrogen or hydrogen.

The thus obtained $N_1$-hydroxybenzoyl-$N_2$-phenyl-1,3-diaminopropan-2-ols of formula (I) can be transformed into the compounds of formula (I) wherein the substituents of the benzoyl group are the above-defined ether groups by reacting an alkali metal salt of the $N_1$-hydroxybenzoyl compounds with an alkyl halogenate, an alkenyl halogenate, an alkinyl halogenate, or a benzoyl halogenate in the presence of a lower alkyl alcohol at a temperature of between about 30° and about 100° C., optionally in a closed reaction vessel under a protective inert gas atmosphere.

Compounds of formula (I) which have been prepared according to the above methods and wherein $R_4$ represents hydrogen can subsequently be alkylated in a conventional manner to obtain the corresponding compounds of formula (I) wherein $R_4$ is alkyl, in particular methyl or ethyl.

The alkylation can be performed by conventional methods which are known from prior art literature, e.g., the reaction with a lower aldehyde under reducing conditions by the method according to Leuckart-Wallach or to Eschweiler-Clarke (see H. Krauch, W. Kunz, Reaktionen der organischen Chemie (1976, p. 131) or by alkylation with dialkylsulfate (see Houben-Weyl, XI/1 (1957, p. 207).

Pharmaceutically acceptable non-toxic acid addition salts of the compounds of formula (I) can be prepared in conventional manner by reacting the free base of formula (I) with an appropriate acid. Suitable acids are, e.g., mineral acids, such as sulfuric acid, hydrochloric acid, hydrobromic acid, nitric acid, or orthophosphoric acid, or organic acids, such as, e.g., p-toluenesulfonic acid, or cyclohexylaminosulfonic acid.

Equally, acid addition salts of compounds of formula (I) can be converted into the free base according to conventional methods.

Compounds of formula (I) wherein at least one of the substituents $R_1$, $R_2$ and $R_3$ represents hydroxy can form salts with pharmaceutically acceptable cations. Since pharmacologically acceptable metal-oxide compounds can, for example, be prepared by reacting an $N_1$-hydroxybenzoyl-$N_2$-phenyl-1,3-diaminpropan-2-ol of formula (I) wherein at least one of the substituents $R_1$, $R_2$ and $R_3$ is hydroxy with an alkali metal or an alkaline-earth metal alcoholate in the presence of a lower alcohol, optionally under protective inert gas atmosphere; or by reacting the $N_1$-hydroxybenzoyl-$N_2$-phenyl-1,3-diaminopropan-2-ol of formula (I) with a hydroxo-metal salt or a metal salt such as metal chloride or metal sulfate in glacial acetic acid/water at a temperature of between about 30° and about 80° C. Suitable pharmacologically acceptable metal salts are, for example, sodium-, magnesium-, zinc-, copper-, alluminum- or bismuth.

The starting materials of formula (II) may be prepared in a conventional manner, e.g., according to the method which is described by M. Chadwick et al. in J. Med. Chem. 9, p. 874 (1966).

The following non-limiting examples are intended to further illustrate the present invention.

EXAMPLE 1

A solution of 38 gr of 3,4,5-trimethoxybenzoyl chloride in 50 ml of chloroform is dropwise added to a solution of 32.7 gr of $N_1$-methyl-$N_1$-(4-fluorophenyl)-1,3-diaminopropan-2-ol and 18.1 gr of triethylamine in 400 ml of chloroform under agitation at ambient temperature. After allowing the reaction mixture to stand for 12 hours, water is added. Subsequently, the organic phase is separated, washed with water and dried over sodium sulfate. After filtering the solution and evaporating the solvent under vacuum, the resulting residue is crystallized from aceton/petrolether. 62.6 g of $N_1$-(3,4,5-trimethoxybenzoyl)-$N_2$-methyl-$N_2$-(4-fluorophenyl)-1,3-diaminopropan-2-ol having a melting point of 113°–116° C. are obtained.

EXAMPLE 2

A mixture of 5.1 g of 3,4,5-trimethoxybenzoylchloride, 100 ml of dioxane, 4.0 g of $N_1$-methyl-$N_1$-(4-fluorophenyl)-1,3-diaminopropan-2-ol and 2.8 g of potassium carbonate is agitated for a period of 12 hours. After filtering the reaction mixture and evaporating the solvent from the filtered solution under vacuum, the remaining residue is heated together with 50 ml of methanol and 15 ml of a 10% sodium hydroxide solution to a temperature of 60° C. for a period of 1 hour. The solvent then is evaporated under vacuum. The residue is re-dissolved in chloroform and isolated. After crystallizing the resulting compound from aceton/petrolether, 5.5 g of crystalline $N_1$-(3,4,5-trimethoxybenzoyl)-$N_2$-methyl-$N_2$-(4-fluorophenyl)-1,3-diaminopropan-2-ol having a melting point of 113°–116° C. are obtained.

EXAMPLE 3

A mixture of 4.0 g of $N_1$-methyl-$N_1$-(4-fluorophenyl)-1,3-diaminopropan-2-ol, 5.1 g of 3,4,5-trimethoxybenzoylchloride and 100 ml of benzene are heated under reflux for a period of 6 hours. Subsequently, 20 ml of an aqueous 20% sodium hydroxide solution are added and thoroughly mixed therewith at a temperature of about 60° C. for a period of 1.5 hours. After working up the reaction mixture and crystallizing the resulting compound from acetone/petrolether, 6.0 g of $N_1$-(3,4,5-trimethoxybenzoyl)-$N_2$-methyl-$N_2$-(4-fluorophenyl)-1,3-diaminopropan-2-ol havin a melting point of 113°–116° C. are obtained.

EXAMPLE 4

5.3 g of 3,4,5-trimethoxybenzoic acid are dissolved in a mixture of 40 ml of chloroform and 2.8 g of triethylamine. 3.0 g of chloroformic acid ethylester are added at a temperature of between 0° and 5° C. After 30 minutes the reaction mixture is cooled to −10° C. and a solution of 5.0 g of $N_1$-methyl-$N_1$-(4-fluorophenyl)-1,3-diaminopropan-2-ol in 50 ml of chloroform is added. The temperature is again allowed to rise to 0° to 10° C. After a period of 2 hours the solution is worked up. The resulting raw product is chromatographically purified using aluminum oxide (activity degree II) as adsorbant and a mixture of chloroform/toluene as eluant and the resulting product is crystallized from acetone-petrolether. 7.8 g of $N_1$-(3,4,5-trimethoxybenzoyl)-$N_2$-methyl-$N_2$-(4-fluorophenyl)-1,3-diaminopropan-2-ol having a melting point of 113°–116° C. are obtained.

EXAMPLE 5

A mixture of 1.9 g of $N_1$-methyl-$N_1$-(4-fluorophenyl)-1,3-diaminopropan-2-ol, 2.3 g of 3,4,5-trimethoxybenzoic acid methylester and 0.4 g of pulverized sodium hydroxide in 50 ml of xylene are heated under reflux for a period of 1 hour. After filtering the reaction mixture and evaporating the solvent, 2.4 g of $N_1$-(3,4,5-trimethoxybenzoyl)-$N_2$-methyl-$N_2$-(4-fluorophenyl)-1,2-diaminopropan-2-ol are obtained. The product is purified by filtration over aluminum oxide (activity degree II) using a mixture of toluene/methylene chloride as eluant and is crystallized from acetone/petrolether, melting point 113°–116° C.

EXAMPLE 6

In the same manner as described in Examples 1 to 3 4-methoxy-3,5-dibenzyloxy-benzoylchloride and $N_1$-methyl-$N_1$-(4-chlorophenyl)-1,3-diaminopropan-2-ol are reacted at $N_1$-(4-methoxy-3,5-dibenzyloxy-benzoyl)-$N_2$-methyl-$N_2$-(4-chlorophenyl)-1,3-diaminopropan-2-ol having a melting point of 155°–158° C. is obtained.

EXAMPLE 7

According to the reaction conditions described in Examples 1 to 5, a 3,4,5-trimethoxybenzoyl derivative of formula (II) is reacted with
(1) N-phenyl-1,3-diaminopropan-2-ol
(2) N-(2-fluuorophenyl)-1,3-diaminopropan-2-ol
(3) N-(3-fluorophenyl)-1,3-diaminopropan-2-ol
(4) N-(4-fluorophenyl)-1,3-diaminopropan-2-ol
(5) N-(2-chlorophenyl)-1,3-diaminopropan-2-ol
(6) N-(2-methylphenyl)-1,3-diaminopropan-2-ol
(7) N-(3-methylphenyl)-1,3-diaminopropan-2-ol
(8) N-(3,4-dichlorophenyl)-1,3-diaminopropan-2-ol (9) N-(3-chloro-2-methylphenyl)-1,3-diaminopropan-2-ol
(10) N-(2,6-dimethylphenyl)-1,3-diaminopropan-2-ol
(11) $N_1$-methyl-$N_1$-(4-chlorophenyl)-1,3-diaminopropan-2-ol
(12) $N_1$-methyl-$N_1$-(4-bromophenyl)-1,3-diaminopropan-2-ol
(13) $N_1$-methyl-$N_1$-(4-methylphenyl)-1,3-diaminopropan-2-ol
(14) $N_1$-methyl-$N_1$-(4-isopropylphenyl)-1,3-diaminopropan-2-ol
(15) $N_1$-methyl-$N_1$-(4-trifluoromethylphenyl)-1,3-diaminopropan-2-ol
(16) $N_1$-methyl-$N_1$-(4-nitrophenyl)-1,3-diaminopropan-2-ol
(17) $N_1$-methyl-$N_1$-(3-methoxyphenyl)-1,3-diaminopropan-2-ol
(18) $N_1$-methyl-$N_1$-(3,4-dichlorophenyl)-1,3-diaminopropan-2-ol
(19) $N_1$-methyl-$N_1$-(3,4-dimethoxyphenyl)-1,3-diaminopropan-2-ol
(20) $N_1$-ethyl-$N_1$-phenyl-1,3-diaminopropan-2-ol
(21) $N_1$-ethyl-$N_1$-(4-fluorophenyl)-1,3-diaminopropan-2-ol
(22) $N_1$-propyl-$N_1$-phenyl-1,3-diaminopropan-2-ol
(23) $N_1$-propyl-$N_1$-(4-chlorophenyl)-1,3-diaminopropan-2-ol
(24) $N_1$-isopropyl-$N_1$-phenyl-1,3-diaminopropan-2-ol
(25) $N_1$-($\beta$-hydroxyethyl)-$N_1$-phenyl-1,3-diaminopropan-2-ol
(26) $N_1$-($\beta$-methoxyethyl)-$N_1$-(4-chlorophenyl)-1,3-diamiopropan-2-ol
(27) N-(2,4,6-trimethylphenyl)-1,3-diaminopropan-2-ol
(28) $N_1$-methyl-$N_2$-(4-ethylphenyl)-1,3-diaminopropan-2-ol and the following comounds are obtained:

|  | mp °C. |
|---|---|
| (1) $N_1$-(3,4,5-trimethoxybenzoyl)-$N_2$-phenyl-1,3-diaminopropan-2-ol | 163–168 |
| (2) $N_1$-(3,4,5-trimethoxybenzoyl)-$N_2$-(2-fluorophenyl)-1,3-diaminopropan-2-ol | 125–130 |
| (3) $N_1$-(3,4,5-trimethoxybenzoyl)-$N_2$-(3-fluorophenyl)-1,3-diaminopropan-2-ol | 155–159 |
| (4) $N_1$-(3,4,5-trimethoxybenzoyl)-$N_2$-(4-fluorophenyl)-1,3-diaminopropan-2-ol | 168–171 |
| (5) $N_1$-(3,4,5-trimethoxybenzoyl)-$N_2$-(2-chlorophenyl)-1,3-diaminopropan-2-ol | 106–108 |
| (6) $N_1$-(3,4,5-trimethoxybenzoyl)-$N_2$-(2-methylphenyl)-1,3-diaminopropan-2-ol | 122–125 |
| (7) $N_1$-(3,4,5-trimethoxybenzoyl)-$N_2$-(3-methylphenyl)-1,3-diaminopropan-2-ol | 137–139 |
| (8) $N_1$-(3,4,5-trimethoxybenzoyl)-$N_2$-(3,4-dichlorophenyl)-1,3-diaminopropan-2-ol | 158–161 |
| (9) $N_1$-(3,4,5-trimethoxybenzoyl)-$N_2$-(3-chloro-2-methylphenyl)-1,3-diaminopropan-2-ol | 135–136 |
| (10) $N_1$-(3,4,5-trimethoxybenzoyl)-$N_2$-(2,6-dimethylphenyl)-1,3-diaminopropan-2-ol | 81–84 |
| (11) $N_1$-(3,4,5-trimethoxybenzoyl)-$N_2$-methyl-$N_2$-(4-chlorophenyl)-1,3-diaminopropan-2-ol | 127–129 |
| (12) $N_1$-(3,4,5-trimethoxybenzoyl)-$N_2$-methyl-$N_2$-(4-bromophenyl)-1,3-diaminopropan-2-ol | 132–134 |
| (13) $N_1$-(3,4,5-trimethoxybenzoyl)-$N_2$-methyl-$N_2$-(4-methylphenyl)-1,3-diaminopropan-2-ol | 135–137 |
| (14) $N_1$-(3,4,5-trimethoxybenzoyl)-$N_2$-methyl-$N_2$-(4-isopropylphenyl)-1,3-diaminopropan-2-ol | 137–139 |
| (15) $N_1$-(3,4,5-trimethoxybenzoyl)-$N_2$-methyl-$N_2$-(4-trifluoromethylphenyl)-1,3-diaminopropan-2-ol | 144–146 |

-continued

| | mp °C. |
|---|---|
| (16) N₁-(3,4,5-trimethoxybenzoyl)-N₂-methyl-N₂-(4-nitrophenyl)-1,3-diaminopropan-2-ol | 172–175 |
| (17) N₁-(3,4,5-trimethoxybenzoyl)-N₂-methyl-N₂-(3-methoxyphenyl)-1,3-diaminopropan-2-ol | 148–150 |
| (18) N₁-(3,4,5-trimethoxybenzoyl)-N₂-methyl-N₂-(3,4-dichlorophenyl)-1,3-diaminopropan-2-ol | 140–143 |
| (19) N₁-(3,4,5-trimethoxybenzoyl)-N₂-methyl-N₂-(3,4-dimethoxyphenyl)-1,3-diaminopropan-2-ol | 69–74 |
| (20) N₁-(3,4,5-trimethoxybenzoyl)-N₂-ethyl-N₂-phenyl-1,3-diaminopropan-2-ol | 114–115 |
| (21) N₁-(3,4,5-trimethoxybenzoyl)-N₂-ethyl-N₂-(4-fluorophenyl)-1,3-diaminopropan-2-ol | 113–116 |
| (22) N₁-(3,4,5-trimethoxybenzoyl)-N₂-propyl-N₂-phenyl-1,3-diaminopropan-2-ol | 111–114 |
| (23) N₁-(3,4,5-trimethoxybenzoyl)-N₂-propyl-N₂-(4-chlorophenyl)-1,3-diaminopropan-2-ol | 140–142 |
| (24) N₁-(3,4,5-trimethoxybenzoyl)-N₂-isopropyl-N₂-phenyl-1,3-diaminopropan-2-ol | Oil* |
| (25) N₁-(3,4,5-trimethoxybenzoyl)-N₂-(β-hydroxyethyl)-N₂-phenyl-1,3-diaminopropan-2-ol | 100–102 |
| (26) N₁-(3,4,5-trimethoxybenzoyl)-N₂-(β-methoxyethyl)-N₂-(4-chlorophenyl)-1,3-diaminopropan-2-ol | 105–108 |
| (27) N₁-(3,4,5-trimethoxybenzoyl)-N₂-(2,4,6-trimethylphenyl)-1,3-diaminopropan-2-ol | 102–104 |
| (28) N₁-(3,4,5-trimethoxybenzoyl)-N₂-methyl-N₂-(4-ethylphenyl)-1,3-diaminopropan-2-ol | 110–114 |

*IR-spectrum (oil) cm⁻¹: 3350 (NH/OH); 1640 (NC = O)

EXAMPLE 8

Under the reaction conditions described in Examples 1 to 3, N₁-methyl-N₁(4-fluorophenyl)-1,3-diaminopropan-2-ol is reacted with the following compounds:
(1) 2,3,4-trimethoxybenzoylchloride,
(2) 2,4,5-trimethoxybenzoylchloride,
(3) 3,4,5-triethoxybenzoylchloride
(4) 4-methoxy-3,5-dibenzyloxybenzoylchloride,
(5) 3,4,5-tribenzyloxybenzoylchloride,
(6) 4-acetoxy-3,5-dimethoxybenzoylchloride,
(7) 4-ethoxycarbonyloxy-3,5-dimethoxybenzoylchloride,
(8) 2-methoxy-4,5-methylenedioxybenzoylchloride,
(9) 4-methoxy-2,3-ethylenedioxybenzoylchloride,
(10) 4-ethoxy-2,3-ethylenedioxybenzoylchloride,
(11) 3-methoxy-4,5-ethylenedioxybenzoylchloride, or
(12) 3-ethoxy-4,5-ethylenedioxybenzoylchloride
and the following compounds are obtained:

| | mp °C. |
|---|---|
| (1) N₁-(2,3,4-trimethoxybenzoyl)-N₂-methyl-N₂-(4-fluorophenyl)-1,3-diaminopropan-2-ol | 84–85 |
| (2) N₁-(2,4,5-trimethoxybenzoyl)-N₂-methyl-N₂-(4-fluorophenyl)-1,3-diaminopropan-2-ol | 131–133 |
| (3) N₁-(3,4,5-triethoxybenzoyl)-N₂-methyl-N₂-(4-fluorophenyl)-1,3-diaminopropan-2-ol | 90–95 |
| (4) N₁-(4-methoxy-3,5-dibenzyloxybenzoyl)-N₂-methyl-N₂-(4-fluorophenyl)-1,3-diaminopropan-2-ol | 137–139 |
| (5) N₁-(3,4,5-tribenzyloxybenzoyl)-N₂-methyl-N₂-(4-fluorophenyl)-1,3-diaminopropan-2-ol | 123–126 |
| (6) N₁-(4-acetoxy-3,5-dimethoxybenzoyl)-N₂-methyl-N₂-(4-fluorophenyl)-1,3-diaminopropan-2-ol | Oil* |
| (7) N₁-(4-ethoxycarbonyloxy-3,5-dimethoxybenzoyl)-N₂-methyl-N₂-(4-fluorophenyl)-1,3-diaminopropan-2-ol, IR-spectrum (oil) cm⁻¹:3360 (NH/OH), 1760 (OC = O); 1640 (NC = O) | Oil |
| (8) N₁-(2-methoxy-4,5-methylenedioxybenzoyl)-N₂-methyl-N₂-(4-fluorophenyl)-1,3-diaminopropan-2-ol, IR-spectrum (oil) cm⁻¹:3380 (NH/OH); 1640 (NC = O) | Oil |
| (9) N₁-(4-methoxy-2,3-ethylenedioxybenzoyl)-N₂-methyl-N₂-(4-fluorophenyl)-1,3-diaminopropan-2-ol | 152–154 |
| (10) N₁-(4-ethoxy-2,3-ethylenedioxybenzoyl)-N₂-methyl-N₂-(4-fluorophenyl)-1,3-diaminopropan-2-ol | 104–107 |
| (11) N₁-(3-methoxy-4,5-ethylenedioxybenzoyl)-N₂-methyl-N₂-(4-fluorophenyl)-1,3-diaminopropan-2-ol | 118–120 |
| (12) N₁-(3-ethoxy-4,5-ethylenedioxybenzoyl)-N₂-methyl-N₂-(4-fluorophenyl)-1,3-diaminopropan-2-ol | 151–157 |

*IR-spectrum (oil) cm⁻¹:3380 (NH/OH); 1765 (OC = O); 1640 (NC = O)

EXAMPLE 9

A mixture of 2.1 g of 2-methoxy-4,5-methylenedioxybenzoic acid ethylester, 9.3 g of N₁-methyl-N₁-(4-fluorophenyl)-1,3-diaminopropan-2-ol and 0.4 g of pulverized sodium hydroxide is heated to a temperature of 130° C. for a period of 2 hours. Chloroform is added to the reaction mixture, unsoluble components are filtered off and the filtrate is chromatographically purified, using aluminum oxide (activity degree II) and chloroform. 1.2 g N₁-(2-methoxy-4,5-methylenedioxybenzoyl)-N₂-methyl-N₂-(4-fluorophenyl)-1,3-diaminopropan-2-ol are obtained as an oil. IR-spectrum (oil) cm⁻¹: 3380 (NH/OH); 1640 (NC=O).

EXAMPLE 10

A mixture of 1.9 g of N₁-(3,4,5-trimethoxybenzoyl)-N₂-(4-fluorophenyl)-1,3-diaminopropan-2-ol, 7.6 ml of formic acid and 2 ml of an aqueous 36% formaldehyde solution is heated for 3 hours on a water-bath. Subsequently, ice is added to the reaction mixture and the reaction mixture is rendered alkaline by addition of diluted sodium hydroxide solution. Chloroform is added and subsequently the compound is recovered from the chloroform phase, and is purified by chromatography on aluminum oxide (activity degree II) using a mixture of methylene chloride/chloroform as eluant. After crystallization from acetone/petrolether, 1.1 g of N₁-(3,4,5-trimethoxybenzoyl)-N₂-methyl-N₂-(4-fluorophenyl)-1,3-diaminopropan-2-ol having a melting point of 113°–116° C. are obtained.

EXAMPLE 11

1.9 g of N₁-(3,4,5-trimethoxybenzoyl)-N₂-(4-fluorophenyl)-1,3-diaminopropan-2-ol are dissolved in 30 ml of dioxane. A mixture of 1.5 g of sodium bicarbonate and 2.5 ml of water are added and then 1.6 ml of dimethyl sulfate are added and the reaction mixture is heated to 60° C. for a period of 1 hour. Subsequently, 10 ml of a 15% sodium hydroxide solution are stirred into the reaction mixture, the solvent is evaporated under vacuum, chloroform is added and the compound is recovered from the chloroform phase.

1.2 g of N₁-(3,4,5-trimethoxybenzoyl)-N₂-methyl-N₂-(4-fluorophenyl)-1,3-diaminopropan-2-ol are obtained. After crystallization from acetone/petrolether the compound has a melting point of 113°–116° C.

EXAMPLE 12

3.6 g of N₁-(3,4,5-trimethoxybenzoyl)-N₂-phenyl-1,3-diaminopropan-2-ol are dissolved in 60 ml of dioxane. A mixture of 3.0 g of sodium bicarbonate and 6 ml of water is added, then 4.4 ml of diethyl sulfate are added and the reaction mixture is heated to a temperature of 60° C. for a period of 0.5 hours. Subsequently, 5 ml of a 15% sodium hydroxide solution are added, the solvent is evaporated under vacuum, chloroform is added and the compound is recovered from the chloroform phase. After chromatographically purifying the compound, using aluminum oxide (activity degree II) and methylene chloride, 2.5 g of $N_1$-(3,4,5-trimethoxybenzoyl)-$N_2$-ethyl-$N_2$-phenyl-1,3-diaminopropan-2-ol are obtained. After crystallization from isopropanol, the compound has a melting point of 114°–115° C.

EXAMPLE 13

24.8 g of $N_1$-(3,4,5-tribenzyloxybenzoyl)-$N_2$-methyl-$N_2$-(4-fluorophenyl)-1,3-diaminopropan-2-ol are dissolved in 1000 ml methanol and are hydrogenated under atmospheric pressure in the presence of 2 g of 5% palladium/charcoal. After removing the catalyst and the solvent, 13 g of $N_1$-(3,4,5-trihydroxybenzoyl)-$N_2$-methyl-$N_2$-(4-fluorophenyl)-1,3-diaminopropan-2-ol, having a melting point of 167°–169° C. are crystallized from ethylacetate/petrolether. Analogously, from the hydrogenation of 10.5 g of $N_1$-(4-methoxy-3,5-dibenzyloxybenzoyl)-$N_2$-methyl-$N_2$-(4-fluorophenyl)-1,3-diaminopropan-2-ol, 6.3 g of $N_1$-(4-methoxy-3,5-dihydroxybenzoyl)-$N_2$-methyl-$N_2$-(4-fluorophenyl)-1,3-diaminopropan-2-ol, having a melting point of 170°–172° C. are obtained; and from the hydrogenation of $N_1$-(4-methoxy-3,5-dibenzyloxybenzoyl)-$N_2$-methyl-$N_2$-(4-chlorophenyl)-1,3-diaminopropan-2-ol the $N_1$-(4-methoxy-3,5-dihydroxybenzoyl)-$N_2$-methyl-$N_2$-(4-chlorophenyl)-1,3-diaminopropan-2-ol are obtained as an oil.

IR-spectrum (oil) $cm^{-1}$:3200–3400 (NH/OH); 1625 (NC=O).

EXAMPLE 14

77 g of $N_1$-(3,5-dimethoxy-4-acetoxybenzoyl)-$N_2$-methyl-$N_2$-(4-fluorophenyl)-1,3-diaminopropan-2-ol are dissolved in 400 ml of acetone and are mixed with a solution of 8.4 g of sodium hydroxide in 300 ml of water at a temperature of 50° C. The solution is then acidified with diluted hydrochloric acid, the solvent is evaporated under vacuum and the precipitated compound is filtered off and is crystallized from isopropanol. 55 g of $N_1$-(3,5-dimethoxy-4-hydroxybenzoyl)-$N_2$-methyl-$N_2$-(4-fluorophenyl)-1,3-diaminopropan-2-ol having a melting point of 161°–164° C. are obtained. The hydrochloride of the compound has a melting point of 220°–223° C.

EXAMPLE 15

Analogously to the procedure described in Example 14, 2 g of $N_1$-(3,5-dimethoxy-4-ethoxycarbonyloxybenzoyl)-$N_2$-methyl-$N_2$-(4-fluorophenyl)-1,3-diaminopropan-2-ol in 50 ml of methanol are treated with 5 ml of an aqueous solution of ammonia at a temperature of 70° C. for a period of 2 hours and $N_1$-(3,5-dimethoxy-4-hydroxybenzoyl)-$N_2$-methyl-$N_2$-(4-fluorophenyl)-1,3-diaminopropan-2-ol is obtained. After crystallization from isopropanol the compound has a melting point of 161°–164° C.

EXAMPLE 16

A mixture of 3.8 g of $N_1$-(4-hydroxy-3,5-dimethoxybenzoyl)-$N_2$-methyl-$N_2$-(4-fluorophenyl)-1,3-diaminopropan-2-ol and an equivalent amount of sodium methylate (0.23 g of sodium in 50 ml of methanol) and 6.0 g of n-butylbromide are heated under reflux for a period of 16 hours. After evaporating the solvent under vacuum, the reaction product is isolated from chloroform and is purified by filtration over aluminum oxide (degree of activity II) with chloroform. The resulting product is crystallized from ether/petrolether. 2.4 g of $N_1$-(4-butoxy-3,5-dimethoxybenzoyl)-$N_2$-methyl-$N_2$-(4-fluorophenyl)-1,3-diaminopropan-2-ol having a melting point of 87°–90° C. are obtained.

In an analogous manner, $N_1$-(4-hydroxy-3,5-dimethoxybenzoyl)-$N_2$-methyl-$N_2$-(4-fluorophenyl)-1,3-diaminopropan-2-ol is reacted with an equivalent amount of allylbromide, proparglybromide, or 4-chlorobenzylchloride and the following compounds are obtained:

$N_1$-(4-allyloxy-3,5-dimethoxybenzoyl)-$N_2$-methyl-$N_2$-(4-fluorophenyl)-1,3-diaminopropan-2-ol having a melting point of 100°–103° C., $N_1$-(4-propargyloxy-3,5-dimethoxybenzoyl)-$N_2$-methyl-$N_2$-(4-fluorophenyl)-1,3-diaminopropan-2-ol having a melting point of 135°–138° C. and $N_1$-[4-(4-chlorobenzyloxy)-3,5-dimethoxybenzoyl]-$N_2$-methyl-$N_2$-(4-fluorophenyl)-1,3-diaminopropan-2-ol having a melting point of 140°–144° C.

A mixture of $N_1$-(4-hydroxy-3,5-dimethoxybenzoyl)-$N_2$-methyl-$N_2$-(4-fluorophenyl)-1,3-diaminopropan-2-ol and an equivalent amount of sodiummethylate in methanol and an excess amount of isopropylbromide is reacted in an autoclave at a temperature of 90°–95° C. and $N_1$-(4-isopropoxy-3,5-dimethoxybenzoyl)-$N_2$-methyl-$N_2$-(4-fluorophenyl)-1,3-diaminopropan-2-ol, having a melting point of 122°–125° C., is obtained.

EXAMPLE 17

1.9 g of $N_1$-(4-hydroxy-3,5-dimethoxybenzoyl)-$N_2$-methyl-$N_2$-(4-fluorophenyl)-1,3-diaminopropan-2-ol are added to a solution of 0.12 g of sodium in 50 ml of methanol and the solution is heated under reflux for a period of 30 minutes. The solvent is evaporated and the remaining residue is crystallized from isopropanol. The resulting sodium-[$N_1$-(4-oxido-3,5-dimethoxybenzoyl)-$N_2$-methyl-$N_2$-(4-fluorophenyl)-1,3-diaminopropan-2-ol] has a melting point of above 250° C.

EXAMPLE 18

A solution of 2.46 g of $N_1$-(4-hydroxy-3,5-dimethoxybenzoyl)-$N_2$-methyl-$N_2$-(4-fluorophenyl)-1,3-diaminopropan-2-ol in 50 ml of methanol and 0.12 ml of water are added to a solution of 0.079 g of magnesium in 50 ml methanol. After heating the reaction mixture to a temperature of 65° C. for a period of 2 hours, hydroxy-magnesium-($N_1$-(4-oxido-3,5-dimethoxybenzoyl)-$N_2$-methyl-$N_2$-(4-fluorophenyl)-1,3-diaminopropan-2-ol, having a melting point of above 250° C. is obtained.

EXAMPLE 19

1.3 g of $N_1$-(4-hydroxy-3,5-dimethoxybenzoyl)-$N_2$-methyl-$N_2$-(4-fluorophenyl)-1,3-diaminopropan-2-ol are suspended in 50 ml of water. Diluted aqueous sodium oxide solution is added until complete solution of the compound is achieved and then a solution of 0.8 g of copper (II)-sulfate-pentahydrate in 20 ml of water is added and the reaction mixture is allowed to stand at ambient temperature for 3 hours. 1.5 g hydroxy-copper (II)-[$N_1$-(4-oxido-3,5-dimethoxybenzoyl)-$N_2$-methyl-$N_2$-(4-fluorophenyl)-1,3-diaminopropan-2-ol] having a melting point of above 250° C. are obtained.

In an analogous manner in a reaction with zinc (II)-sulfate-heptahydrate, hydroxy-zinc-[$N_1$-(4-oxido-3,5- dimethoxybenzoyl)-$N_2$-methyl-$N_2$-(4-fluorophenyl)-1,3-diaminopropan-2-ol] having a melting point of above 200° C. is obtained.

EXAMPLE 20

A mixture of 2.3 g of basic bismuth (III)-nitrate and 4.0 g of $N_1$-(3,4,5-trihydroxybenzoyl)-$N_2$-methyl-$N_2$-(4-fluorophenyl)-1,3-diaminopropan-2-ol is heated in a mixture of 50 ml of acetic acid and 50 ml of water to a temperature of 65° C. for a period of 2 hours. 3.8 g of hydroxy-bismuth(III)-[$N_1$-(3,4-dioxido-5-hydroxybenzoyl)-$N_2$-methyl-$N_2$-(4-fluorophenyl)-1,3-diaminopropan-2-ol] having a melting point of above 200° C. are obtained.

In an analogous manner in a reaction with aluminum-chloride-hexahydrate, hydroxy-aluminum-[$N_1$-(3,4-dioxido-5-hydroxybenzoyl)-$N_2$-methyl-$N_2$-(4-fluorophenyl)-1,3-diaminopropan-2-ol] having a melting point of above 200° C. are obtained.

EXAMPLE 21

Tablets

Tablets containing 100 mg of $N_1$-(3,4,5-trimethoxybenzoyl)-$N_2$-methyl-$N_2$-(4-fluorophenyl)-1,3-diaminopropan-2-ol as pharmacologically active ingredients are prepared. Composition per tablet:

| | |
|---|---|
| pharmacologically active agent | 100 mg |
| lactose | 60 mg |
| corn starch | 30 mg |
| carboxymethylcellulose (Commercial product Primojel, Manufacturer Scholtens Chemische Fabricken N.V.) | 4 mg |
| gelatin | 2 mg |
| highly dispersed silicic acid (Commercial product Aerosil 200, Manufacturer Degussa) | 2 mg |
| magnesium stearate | 2 mg |
| | 200 mg |

Preparation: A 10% mucilage of gelatin in water is prepared. The pharmacologically active agent, lactose, corn starch, and carboxymethylcellulose, are mixed, the mixture is then mixed with the mucilage and granulated through a sieve of 1.5 mm mesh-size. The granulate is dried at 40° C., once more passed through the sieve, mixed with the highly dispersed silicic acid, and the magnesium stearate and the mixture pressed into tablets using a die having a diameter of 9 mm.

What is claimed is:

1. A method for treating and prophylaxis of acute and chronic gastritis in larger mammals, which comprises the step of orally administering to a larger mammal an effective amount of at least one compound said compound being selected from the group of $N_1$-benzoyl-$N_2$-phenyl-1,3-diaminopropan-2-ols having the formula I

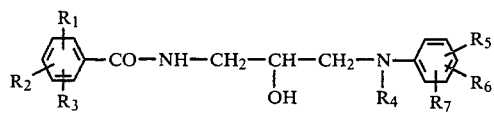

wherein $R_1$, $R_2$ and $R_3$ are the same or different from each other and each represents hydroxy, benzyloxy, chlorbenzyloxy or alkoxy containing 1 to 4 carbon atoms, or $R_1$ is as defined above and $R_2$ and $R_3$ together represent methylenedioxy and ethylenedioxy, or $R_1$ and $R_2$ represent methoxy and $R_3$ represents allyloxy or propargyloxy;

$R_4$ represents hydrogen, alkyl containing 1 to 4 carbon atoms, $\beta$-hydroxytehyl, or $\beta$-methoxyethyl, and $R_5$, $R_6$ and $R_7$ are the same or different from each other and $R_5$ and $R_6$ each represents hydrogen, fluorine, chlorine, bromine, iodine, alkyl containing 1 to 4 carbon atoms, or alkoxy containing 1 to 4 carbon atoms; or $R_5$ and $R_6$ together represent methylenedioxy or ethylenedioxy, and $R_7$ represents hydrogen, fluorine, chlorine, bromine, iodine, alkyl containing 1 to 4 carbon atoms, alkoxy containing 1 to 3 carbon atoms, trifluoromethyl or nitro;

with the proviso that if $R_1$, $R_2$ and $R_3$ each represents methoxy and is situated in 3, 4 and 5 position and $R_4$ is methyl, no more than 2 of the substituents $R_5$, $R_6$ and $R_7$ represent hydrogen, and pharmaceutically acceptable salts thereof.

2. A method of stabilizing the gastro-intestinal mucosa against gastritis-producing effects in larger mammals, which comprises the step of orally administering to a larger mammal an effective stabilizing amount of at least one compound, said compound being selected from the group of $N_1$-benzoyl-$N_2$-phenyl-1,3-diaminopropan-2-ols having the formula I

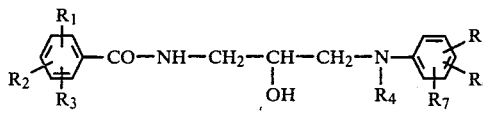

wherein $R_1$, $R_2$ and $R_3$ are the same or different from each other and each represents hydroxy, benzyloxy, chlorbenzyloxy or alkoxy containing 1 to 4 carbon atoms, or $R_1$ is as defined above and $R_2$ and $R_3$ together represent methylenedioxy and ethylenedioxy, or $R_1$ and $R_2$ represent methoxy and $R_3$ represents allyloxy or propargyloxy;

$R_4$ represents hydrogen, alkyl containing 1 to 4 carbon atoms, $\beta$-hydroxyethyl, or $\beta$-methoxyethyl, and $R_5$, $R_6$ and $R_7$ are the same or different from each other and $R_5$ and $R_6$ each represents hydrogen, fluorine, chlorine, bromine, iodine, alkyl containing 1 to 4 carbon atoms, or alkoxy containing 1 to 4 carbon atoms; or $R_5$ and $R_6$ together represent methylenedioxy or ethylenedioxy, and $R_7$ represents hydrogen, fluorine, chlorine, bromine, iodine, alkyl containing 1 to 4 carbon atoms, alkoxy containing 1 to 3 carbon atoms, trilfuoromethyl or nitro;

with the priviso that if $R_1$, $R_2$ and $R_3$ each represents methoxy and is situated in 3, 4 and 5 position and $R_4$ is methyl, no more than 2 of the substituents $R_5$, $R_6$ and $R_7$ represent hydrogen, and pharmaceutically acceptable salts thereof.

3. A method as defined in claim 1 or 2 wherein said compound is a pharmaceutically acceptable acid addition salt of a $N_1$-benzoyl-$N_2$-phenyl-1,3-diaminopropan-2-ol of formula I.

4. A method as defined in claim 1 or 2 wherein said compound is a salt of a $N_1$-benzoyl-$N_2$-phenyl-1,3-diaminopropan-2-ol of formula I, wherein at least one of the substituents $R_1$, $R_2$ and $R_3$ is hydroxy with a pharmaceutically acceptable cation.

5. A method as defined in claim 1 or 2, wherein the group

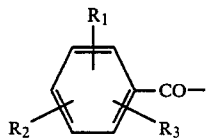

represents 3,4,5-trimethoxybenzoyl.

6. A method as defined in claim 5, wherein the group

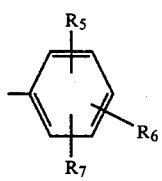

represents phenyl; 2-fluorophenyl, 3-fluorophenyl, 4-fluorophenyl, 2-chlorophenyl, 2-methylphenyl, 3-methylphenyl, 3,4-dichlorophenyl, 3-chloro-2-methylphenyl, 2,6-dimethylphenyl, or 2,4,6-trimethylphenyl, and $R_4$ represents hydrogen.

7. A method as defined in claim 5, wherein the group

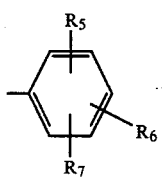

represents 4-fluorophenyl, 4-chlorophenyl, 4-bromophenyl, 4-methylphenyl, 4-ethylphenyl, 4-isopropylphenyl, 4-trifluoromethylphenyl, 3-methoxyphenyl, 3,4-dichlorophenyl, 3,4-dimethoxyphenyl or 4-nitrophenyl, and $R_4$ represents methyl.

8. A method as defined in claim 3, wherein $R_4$ represents ethyl, propyl, isopropyl or β-hydroxyethyl, and the group

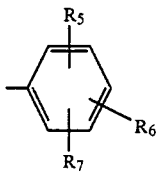

represents phenyl.

9. A method as defined in claim 3, wherein the group

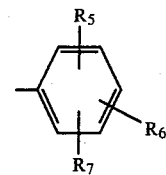

represents 4-chlorophenyl, and $R_4$ represents propyl or β-methoxyethyl.

10. A method as defined in claim 4, wherein said compound is $N_1$-(3,4,5-trimethoxybenzoyl)-$N_2$-ethyl-$N_2$-(4-fluorophenyl)-1,3-diaminopropan-2-ol and its pharmaceutically acceptable acid addition salts.

11. A method as defined in claim 1 or 2 wherein $R_4$ is methyl, the group

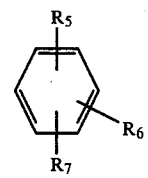

represents 4-fluorophenyl, and the group

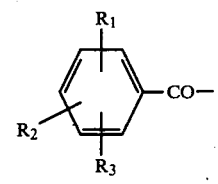

represents 2,3,4-trimethoxybenzoyl, 2,4,5-trimethoxybenzoyl, 3,4,5-triethoxybenzoyl, 4-methoxy-3,5-dibenzyloxybenzoyl, 3,4,5-tribenzyloxybenzoyl, 4-hydroxy-3,5-dimethoxybenzoyl, 4-methoxy-3,5-dihydroxybenzoyl, 3,4,5-trihydroxybenzoyl, 4-isopropoxy-3,5-dimethoxybenzoyl, 4-butoxy-3,5-dimethoxybenzoyl, 4-allyloxy-3,5-dimethoxybenzoyl, 4-propargyloxy-3,5-dimethoxybenzoyl, 4-(4-chlorobenzyloxy)-3,5-dimethoxybenzoyl.

12. A method as defined in claim 1 or 2, wherein $R_4$ is methyl, the group

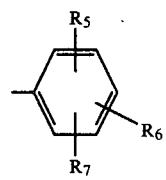

represents 4-chlorophenyl and the group

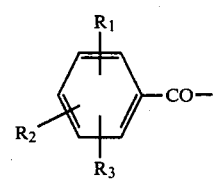

represents 4-methoxy-3,5-dibenzyloxybenzoyl, or 4-methoxy-3,4-dihydroxybenzoyl.

13. The method as defined in claim 1 or 2, wherein the amount of the pharmacologically active compound is from about 150 to about 450 mg per day.

14. A method as defined in claim 1 or 2 wherein said compound is $N_1$-(3,4,5-trimethoxybenzoyl)-$N_2$-methyl-$N_2$-(4-fluorophenyl)-1,3-diaminopropan-2-ol.

15. A method as defined in claim 1 or 2 wherein said compound is $N_1$-(3,4,5-trimethoxybenzoyl)-$N_2$-methyl-$N_2$-(4-chlorophenyl)-1,3-diaminopropan-2-ol.

16. A method as defined in claim 1 or 2, wherein said compound is $N_1$-(3,4,5-trimethoxybenzoyl)-$N_2$-methyl-$N_2$-(4-trifluoromethylphenyl)-1,3-diaminopropan-2-ol.

17. A method as defined in claim 1 or 2, wherein said compound is $N_1$-(3,4,5-trimethoxybenzoyl)-$N_2$-methyl-$N_2$-(4-methylphenyl)-1,3-diaminopropan-2-ol.

18. A method as defined in claim 1 or 2, wherein said compound is $N_1$-(3,4,5-trimethoxybenzoyl)-$N_2$-ethyl-$N_2$-(4-fluorophenyl)-1,3-diaminopropan-2-ol.

19. A method as defined in claim 1 or 2, wherein said compound is $N_1$-(3,4,5-trimethoxybenzoyl)-$N_2$-(2,4,6-trimethylphenyl)-1,3-diaminopropan-2-ol.

20. A method as defined in claim 1 or 2, wherein said compound is $N_1$-(3,4,5-triethoxybenzoyl)-$N_2$-methyl-$N_2$-(4-fluorophenyl)-1,3-diaminopropan-2-ol.

21. A method as defined in claim 1 or 2, wherein said compound is $N_1$-(4-butoxy-3,4-dimethoxybenzoyl)-$N_2$-methyl-$N_2$-(4-fluorophenyl)-1,3-diaminopropan-2-ol.

22. A pharmaceutical composition in dosage form for oral administration comprising an effective amount of from about 50 to 150 mg per single dosage unit of at least one pharmacologically active compound, which is effective in stabilizing the gasto-intestinal mucosa, and a pharmaceutically acceptable diluent, said compound being selected from the group of $N_1$-benzoyl-$N_2$-phenyl-1,3-diaminopropan-2-ols having the formula I

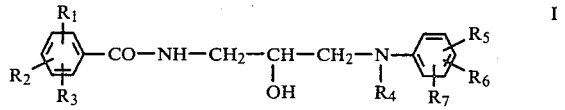

wherein
- $R_1$, $R_2$ and $R_3$ are the same or different from each other and each represents hydroxy, benzyloxy, chlorbenzyloxy or alkoxy containing 1 to 4 carbon atoms, or
- $R_1$ is as defined above and $R_2$ and $R_3$ together represent methylenedioxy and ethylenedioxy, or
- $R_1$ and $R_2$ represent methoxy and $R_3$ represents allyloxy or propargyloxy;
- $R_4$ represents hydrogen, alkyl containing 1 to 4 carbon atoms, β-hydroxyethyl, or β-methoxyethyl, and
- $R_5$, $R_6$ and $R_7$ are the same or different from each other and $R_5$ and $R_6$ each represents hydrogen, fluorine, chlorine, bromine, iodine, alkyl containing 1 to 4 carbon atoms, or alkoxy containing 1 to 4 carbon atoms; or
- $R_5$ and $R_6$ together represent methylenedioxy or ethylenedioxy, and $R_7$ represents hydrogen, fluorine, chlorine, bromine, iodine, alkyl containing 1 to 4 carbon atoms, alkoxy containing 1 to 3 carbon atoms, trifluoromethyl or nitro;

with the proviso that if $R_1$, $R_2$ and $R_3$ each represents methoxy and is situated in 3, 4 and 5 position and $R_4$ is methyl, no more than 2 of the substituents $R_5$, $R_6$ and $R_7$ represent hydrogen, and pharmaceutically acceptable salts thereof.

23. A pharmaceutical composition in dosage unit form for oral administration comprising an effective amount of from about 50 to 100 mg per single dosage unit of at least one pharmacologically active compound, which is effective against gastritis, and a pharmaceutically acceptable diluent, said compound being selected from the group of $N_1$-benzoyl-$N_2$-phenyl-1,3-diaminopropan-2-ols having the formula I

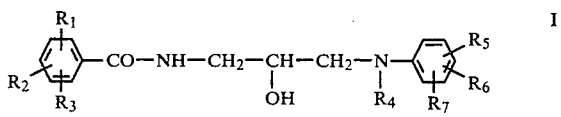

wherein
- $R_1$, $R_2$ and $R_3$ are the same or different from each other and each represents hydroxy, benzyloxy, chlorbenzyloxy or alkoxy containing 1 to 4 carbon atoms, or
- $R_1$ is as defined above and $R_2$ and $R_3$ together represent methylenedioxy and ethylenedioxy, or
- $R_1$ and $R_2$ represent methoxy and $R_3$ represents allyloxy or propargyloxy;
- $R_4$ represents hydrogen, alkyl containing 1 to 4 carbon atoms, β-hydroxyethyl, or β-methoxyethyl, and
- $R_5$, $R_6$ and $R_7$ are the same or different from each other and $R_5$ and $R_6$ each represents hydrogen, fluorine, chlorine, bromine, iodine, alkyl containing 1 to 4 carbon atoms, or alkoxy containing 1 to 4 carbon atoms; or
- $R_5$ and $R_6$ together represent methylenedioxy or ethylenedioxy, and $R_7$ represents hydrogen, fluorine, chlorine, bromine, iodine, alkyl containing 1 to 4 carbon atoms, alkoxy containing 1 to 3 carbon atoms, trifluoromethyl or nitro;

with the proviso that if $R_1$, $R_2$ and $R_3$ each represents methoxy and is situated in 3, 4 and 5 position and $R_4$ is methyl, no more than 2 of the substituents $R_5$, $R_6$ and $R_7$ represent hydrogen, and pharmaceutically acceptable salts thereof.

24. The pharmaceutical composition as defined in claim 22 or 23, which is a solid composition.

* * * * *